(12) United States Patent
Lambertz

(10) Patent No.: US 8,505,120 B2
(45) Date of Patent: Aug. 13, 2013

(54) SOCK

(75) Inventor: Bodo W. Lambertz, Pfäffikon (CH)

(73) Assignee: X-Technology Swiss GmbH, Wollerau (CH)

( * ) Notice: Subject to any disclaimer, the term of this patent is extended or adjusted under 35 U.S.C. 154(b) by 268 days.

(21) Appl. No.: 11/988,476

(22) PCT Filed: Jul. 5, 2006

(86) PCT No.: PCT/EP2006/006537
§ 371 (c)(1),
(2), (4) Date: Jan. 8, 2008

(87) PCT Pub. No.: WO2007/006462
PCT Pub. Date: Jan. 18, 2007

(65) Prior Publication Data
US 2009/0126081 A1    May 21, 2009

(30) Foreign Application Priority Data
Jul. 9, 2005  (DE) .......................... 10 2005 032 189

(51) Int. Cl.
*A41B 17/00* (2006.01)

(52) U.S. Cl.
USPC ............................................................ 2/239

(58) Field of Classification Search
USPC .................. 2/239, 240, 241, 409; 66/178 A, 66/180, 183, 188, 189; 602/27, 28; D2/980, D2/981, 982, 985, 986, 988, 992, 994
See application file for complete search history.

(56) References Cited

U.S. PATENT DOCUMENTS

| | | | | |
|---|---|---|---|---|
| 67,264 A | * | 7/1867 | Carey | 66/187 |
| 1,231,443 A | * | 6/1917 | Smith | 66/185 |
| 1,544,934 A | * | 7/1925 | Prankard | 66/188 |
| 1,625,523 A | * | 4/1927 | Butz | 66/182 |
| 1,811,786 A | * | 6/1931 | Frei | 66/187 |
| 2,050,535 A | * | 8/1936 | Martel | 66/178 R |
| 2,102,368 A | * | 12/1937 | Martel | 66/182 |
| 2,188,241 A | * | 1/1940 | Davis | 66/178 A |
| D165,284 S | * | 11/1951 | Hiestand | D2/970 |
| D166,232 S | * | 3/1952 | Torgersen | D2/994 |
| D166,233 S | * | 3/1952 | Torgersen | D2/994 |
| 2,904,980 A | * | 9/1959 | Stinson | 66/171 |
| 3,241,340 A | * | 3/1966 | Knohl | 66/185 |
| 3,443,404 A | * | 5/1969 | Herbert | 66/178 A |
| 3,562,818 A | * | 2/1971 | Burton | 2/239 |
| 3,990,115 A | * | 11/1976 | Nester | 2/239 |
| 4,149,274 A | * | 4/1979 | Garrou et al. | 2/239 |
| 4,169,324 A | * | 10/1979 | Gibbs | 36/83 |
| 4,192,019 A | * | 3/1980 | Lingenfelter | 2/239 |
| D311,448 S | * | 10/1990 | Kemna et al. | D2/980 |

(Continued)

FOREIGN PATENT DOCUMENTS

WO        WO 9918896 A1  *  4/1999

*Primary Examiner* — Alissa L Hoey
(74) *Attorney, Agent, or Firm* — Olson & Cepuritis, Ltd.

(57) ABSTRACT

The invention relates to a sock, especially for use in sports, which comprises a foot part (1) and a leg (2), said foot part having a toe area (11) and a heel area (12) and a sole area (13) between the toe and the heel area, and which is also provided with an O-ring-type bandage (22). An O-ring-type bandage (22) is disposed in the area of the ankle joint and extends asymmetrically on the circumference of the sock.

10 Claims, 4 Drawing Sheets

(56) References Cited

U.S. PATENT DOCUMENTS

| | | | | |
|---|---|---|---|---|
| 5,027,441 A * | 7/1991 | Wilson | | 2/240 |
| 5,103,656 A * | 4/1992 | Hanson, II | | 66/185 |
| 5,139,479 A * | 8/1992 | Peters | | 602/27 |
| 5,399,155 A * | 3/1995 | Strassburg et al. | | 602/28 |
| 5,473,781 A * | 12/1995 | Greenberg | | 2/239 |
| 5,617,745 A * | 4/1997 | Della Corte et al. | | 66/178 A |
| 5,620,413 A * | 4/1997 | Olson | | 602/65 |
| 5,653,128 A * | 8/1997 | Warren et al. | | 66/172 E |
| 5,867,838 A * | 2/1999 | Corry | | 2/239 |
| 5,891,073 A * | 4/1999 | Deirmendjian et al. | | 602/27 |
| 5,898,948 A * | 5/1999 | Kelly et al. | | 2/240 |
| 5,925,010 A * | 7/1999 | Caprio, Jr. | | 602/62 |
| 6,117,098 A * | 9/2000 | Weber et al. | | 602/27 |
| 6,139,929 A * | 10/2000 | Hayton et al. | | 428/35.2 |
| 6,142,967 A * | 11/2000 | Couch | | 602/66 |
| 6,286,151 B1 * | 9/2001 | Lambertz | | 2/239 |
| 6,311,334 B1 * | 11/2001 | Reinhardt et al. | | 2/239 |
| 6,350,247 B2 * | 2/2002 | Bodenschatz et al. | | 602/65 |
| 6,536,051 B1 * | 3/2003 | Oh | | 2/239 |
| 6,564,393 B2 * | 5/2003 | Davies | | 2/239 |
| 6,641,550 B1 * | 11/2003 | Johnson | | 602/65 |
| 6,805,681 B2 * | 10/2004 | Yokoyama | | 602/65 |
| 7,082,703 B2 * | 8/2006 | Greene et al. | | 36/89 |
| 7,192,411 B2 * | 3/2007 | Gobet et al. | | 602/63 |
| 7,740,603 B2 * | 6/2010 | Shoukry | | 602/28 |
| D650,969 S * | 12/2011 | Wong | | D2/624 |
| 2003/0230121 A1 * | 12/2003 | Yokoyama | | 66/178 A |
| 2006/0026740 A1 * | 2/2006 | Vargas et al. | | 2/239 |
| 2006/0085894 A1 * | 4/2006 | Yakopson et al. | | 2/239 |
| 2006/0130217 A1 * | 6/2006 | Lambertz | | 2/239 |
| 2006/0143801 A1 * | 7/2006 | Lambertz | | 2/239 |
| 2006/0195971 A1 * | 9/2006 | Lambertz | | 2/239 |
| 2007/0033710 A1 * | 2/2007 | Lambertz | | 2/239 |
| 2007/0118973 A1 * | 5/2007 | Lambertz | | 2/239 |
| 2007/0179421 A1 * | 8/2007 | Farrow | | 602/75 |
| 2008/0295216 A1 * | 12/2008 | Nordstrom et al. | | 2/69 |
| 2009/0013450 A1 * | 1/2009 | Lambertz | | 2/239 |
| 2009/0018482 A1 * | 1/2009 | Lambertz | | 602/65 |
| 2009/0044313 A1 * | 2/2009 | Anastsopoulos et al. | | 2/241 |
| 2009/0270784 A1 * | 10/2009 | Arensdorf | | 602/27 |
| 2010/0137776 A1 * | 6/2010 | Virkus et al. | | 602/62 |

* cited by examiner

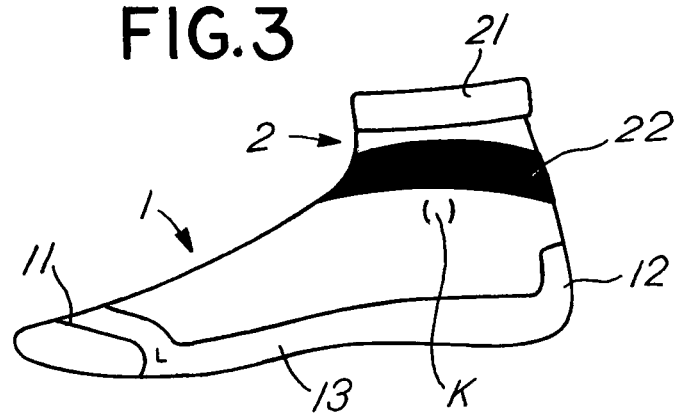
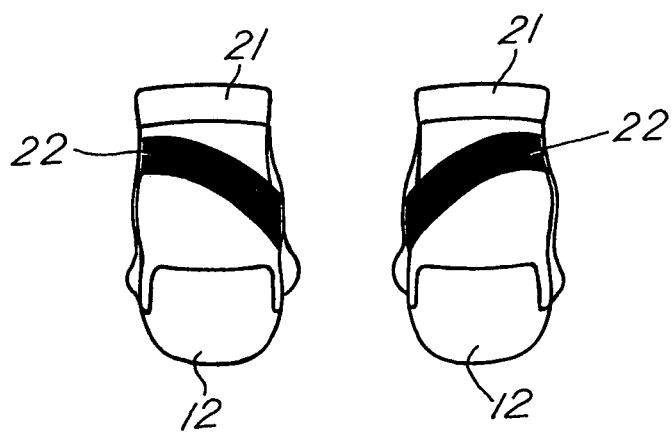

SOCK

This application is the National Stage of International Application No. PCT/EP2006/006537, filed Jul. 5, 2006, which is incorporated herein by reference.

BACKGROUND OF THE INVENTION

The invention pertains to a sock, especially for use in sports activities, with a leg part and a foot part. The foot part has a toe area, a heel area, and a sole area, which is located between the toe and heel areas, the sock being provided with an O-ring bandage.

Especially in the case of sports activities, the human foot is usually enclosed by a sock. So that the sock will fit properly on the foot, it is known that O-ring bandages can be provided on socks or stockings (see, for example, U.S. Pat. No. 5,617, 745). These, however, are arranged to extend circumferentially and symmetrically, and parallel to the longitudinal center line of the sock.

Running and jumping movements exert increased stress on the foot, especially in the area of the ankle. The foot has the natural function of flexing inward to damp such impacts. This function is called pronation. After the outside part of the sole has made contact with the ground, the load shifts somewhat toward the inside, so that the lengthwise arch of the foot can flatten out and thus absorb some of the impact. The human foot, however, can be formed in different ways. Feet can be divided into normal, contracted, inverted, and flat. The normal foot shows a balanced arch. During walking and running, the outside edge of the foot strikes the ground first. Then it rolls inward to absorb and to damp the impact of the foot. This is referred to as "natural pronation". Contracted and inverted feet do not inflect inward for the most part during the landing phase, and the footprint left behind consists primarily of the forward and rear parts of the foot. This is called "underpronation" or "supination". The natural ability of the foot to protect against impact is considerably reduced in the case of underpronation. Flat feet, furthermore, have a very low arch and leave behind a footprint consisting of the complete foot. Flat feet flex very strongly toward the inside after the landing phase. This is called overpronation. In addition, the motor apparatus in the area of the foot joints can be stressed by improper alignment of the legs, which can take either the form commonly called bowlegged or that called knock-kneed.

Both overpronators and underpronators, as well as people with improper alignment of the legs, suffer from the problem of insufficient natural damping. As a result, severe stress is imposed on the foot. To support the ligaments and tendons of the motor apparatus around the ankle, it is known that bandages can be placed around the foot. A bandage is wrapped horizontally around the lower area of the shin and around the ankle before the sock is pulled over the foot. This wrapping, however, does not offer satisfactory stabilization and support of the motor apparatus around the ankle, and in addition it does not take into account the special forms of stress associated with overpronation and underpronation. The bandage, furthermore, adds considerable bulk under the sock, which decreases the wearing comfort.

The invention proposes to provide a remedy to this situation. The invention is based on the task of creating a sock which supports the motion apparatus in the area of the ankle and which is designed specifically to deal with the special stresses which occur in association with overpronation and underpronation and also those associated with misalignment of the legs. According to the invention, this task is accomplished in that at least one O-ring bandage is provided in the area of the ankle, this bandage extending asymmetrically around the circumference of the sock.

The invention creates a sock, especially a sock for sports activities, which supports the motion apparatus in the area of the ankle and which deals specifically with the particular stresses associated with overpronation and underpronation and also with those associated with misalignment of the legs. For this reason, the O-ring bandage is located in the area of the ankle in such a way that it can provide a support function appropriate to the type of stress being imposed in the case in question.

In an embodiment of the invention, the asymmetric O-ring bandage passes under the ankle on the inside of the foot and above the ankle on the outside of the foot. As a result, the ankle is supported in particular against strong forces acting outward.

In another embodiment of the invention, the asymmetric O-ring bandage passes above the ankle on the inside of the foot and under the ankle on the outside of the foot. As a result, the ankle is supported in particular against strong forces acting outward.

In an elaboration of the invention, two O-ring bandages are provided. As a result, the support function provided for the ankle is improved even more. The opposing arrangement of the bandages, furthermore, creates a support function acting on both sides of the ankle.

In an embodiment of the invention, the sock has at least one wicking channel. The wicking channel is used to optimize the temperature and humidity conditions of the foot by conducting away perspiration. To avoid excessive layers of material, the wicking channel preferably passes through the bandages.

Other elaborations and embodiments of the invention are stated in the other subclaims.

BRIEF DESCRIPTION OF THE DRAWING

Exemplary embodiments of the invention are illustrated in the drawings and are described in detail below:

FIG. 3 shows a different design of a sock with an asymmetric O-ring bandage;

FIG. 4 shows a view of a pair of socks of the type according to FIG. 3 from the rear;

DETAILED DESCRIPTION OF THE INVENTION

Figure 1:
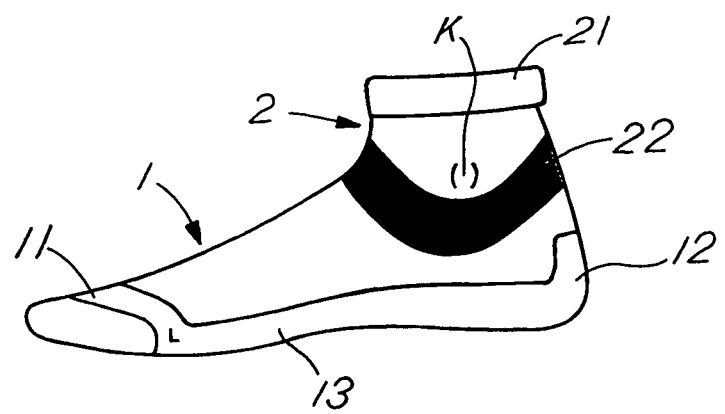
FIG. 1 shows a side view of the outside surface of a foot wearing a sock with an asymmetric O-ring bandage.

The sock selected as the exemplary embodiment (FIG. 1) consists of a foot part 1 and a leg part 2. The foot part 1 has a toe area 11, a heel area 12, and a sole area 13 located between the toe and heel parts. The areas 11, 12, and 13 can be made of reinforced material, as shown in the exemplary embodiment. The use of material combinations such as virgin wool plus elastic fibers is also possible.

The leg part 2 is provided with a collar 21 at the end facing away from the foot part 1. In the ankle area, the sock is provided with an O-ring bandage 22, which extends asymmetrically around the circumference of the sock. The bandage 22 is made of an elastic and also a wicking fabric. Elastan, Lycra, or other materials of varying degrees of stretchability are preferably used.

Figure 2:
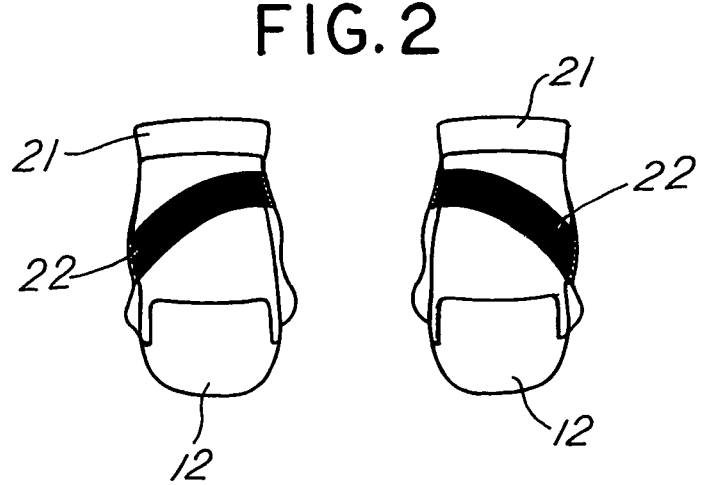
FIG. 2 shows a view of a pair of socks of the type according to FIG. 1 from the rear.

The O-ring bandage 22 is woven all the way around together with the same fabric as that which forms the sock. In the exemplary embodiment shown here according to FIGS. 1 and 2, the O-ring bandage 22 is asymmetric; that is, it passes under the ankle, designated "K", on the outside of the foot and above the ankle on the inside of the foot. In this embodiment, the O-ring bandage 22 supports the ankle and the ligaments arranged around it especially against the effects of forces acting inward on the ankle. Alternatively, the asymmetric O-ring bandage 22 can be designed so that—again in asymmetric fashion—it passes above the ankle on the outside of the foot and below the ankle on the inside of the foot (FIGS. 3 and 4). In this embodiment, it supports the ankle and the ligaments around it especially against the effects of forces acting outward on the ankle.

In the case of the pair of socks shown in FIG. 4, in which the asymmetric O-ring bandage 22 is designed in such a way that it passes above the ankle on the outside of the foot and below the ankle on the inside of the foot, what is obtained when viewed from the rear is the form of a "V". In contrast, what we see when we look at the pair of socks illustrated in FIG. 2 from the rear is the shape of an "A" because of the different arrangement of the asymmetric O-ring bandages 22.

Figure 5:
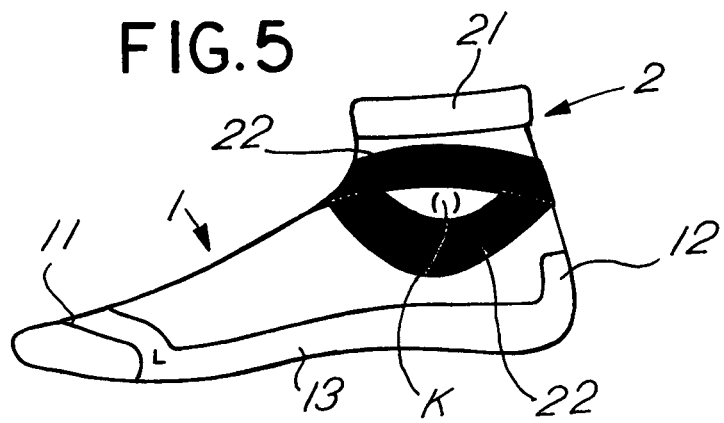
FIG. 5 shows another embodiment of a sock with an asymmetric O-ring bandage.
Figure 6:
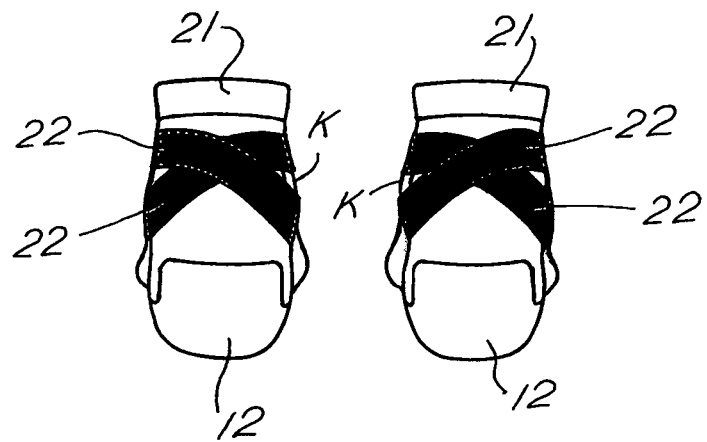
FIG. 6 shows a view of a pair of socks of the type according to FIG. 5 from the rear.

In the exemplary embodiment shown in FIGS. 5 and 6, two O-ring bandages 22 are provided in the sock, as a result of which the supporting action is increased even more. An opposing arrangement of the bandages 22 is selected, so that the bandages 22 cross each other in the area of the Achilles tendon and again in the area of the transition between the top of the foot and the shin. When the pair of socks is seen from the rear, we see that this arrangement of the O-ring bandages 22 produces the form of an "X". As a result of this design, a support function acting on both sides of the ankle is obtained, where the ankle "K" is surrounded by the bandages 22 on both the outside and the inside.

Figure 7:
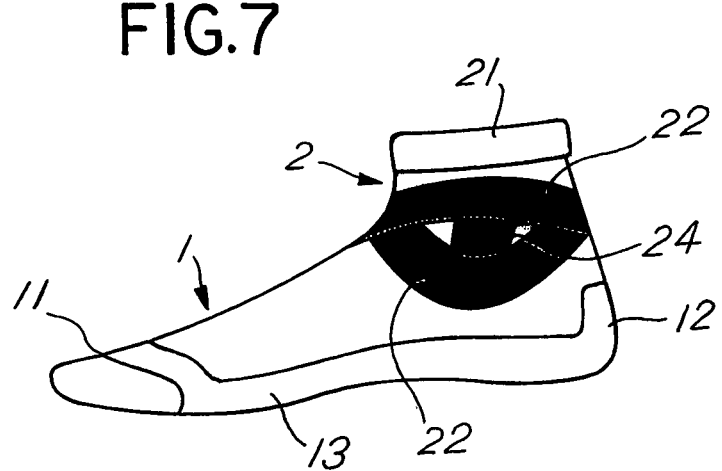
FIG. 7 shows another design of a sock with an asymmetric O-ring bandage.
Figure 8:
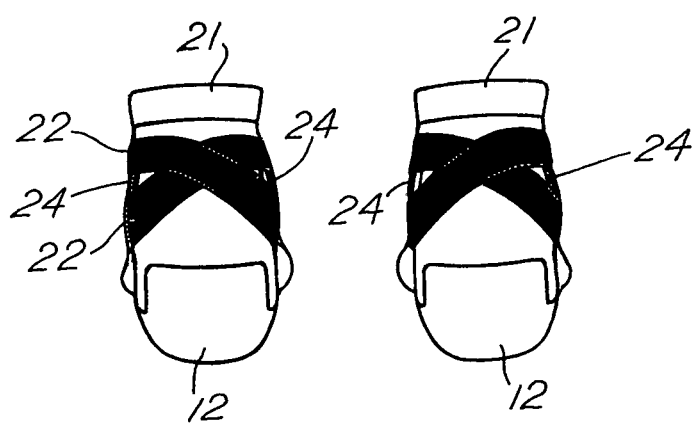
FIG. 8 shows a view of a pair of socks of the type according to FIG. 7 from the rear.

In the exemplary embodiment according to FIGS. 7 and 8, two opposing O-ring bandages 22 are again provided. On the outside of the leg and on the inside of the leg, the bandages 22, which are a certain distance apart here, are connected to each other by a web 24. The webs 24 pass across the ankle "K". The support function is thus improved yet again. In particular, a lateral support function is obtained, which does not hinder the rolling and bending of the foot during running or the like in any way, because the bandages have their narrowest points in the areas where the foot bends—the Achilles tendon and the transition from the top of the foot to the shin.

The sock can be provided with a wicking channel (not shown), which proceeds from the collar 21 and extends as far as the sole area 13 and is formed of mesh knit fabric with a wicking function. The wicking channel helps to carry moisture up and away from the sole area. The asymmetric O-ring bandage 22 is located over the wicking channel. A wicking channel of this type can be provided both on the outside of the leg and on the inside of the leg of the sock.

Inso far as socks have been mentioned in the description and in the claims, the invention is not limited to these alone; on the contrary, the term "sock" is also meant to include stockings, tights, etc. to which the invention also pertains.

The invention claimed is:

1. A sock, to be worn on the foot of a user and covering the ankle of the user, especially for use in sports activities, with a leg part including a first ankle area covering one side of the ankle of the user when worn, and a second ankle area covering the opposite side of the ankle of the user when worn, and a foot part, the foot part having a toe area, a heel area, and a sole area, which is located between the toe area and the heel area, the sock being made from fabric and being provided with an elastic O-ring bandage (22) made of an elastic fabric woven together with the fabric of the sock, the O-ring bandage passing asymmetrically around a circumference of the sock in an ankle region thereof, the O-ring bandage (22) being constructed and arranged to provide a support function for the ankle of the user and ligaments around the ankle of the user when worn, the elastic fabric of the O-ring bandage (22) having greater elasticity than that of the fabric of the sock, so that when the sock is worn, a portion of said O-ring bandage (22) is positioned below the first ankle area and above the sole area on one side of the ankle of the user, and another portion of the O-ring bandage (22) is positioned above the second ankle area covering the opposite side of the ankle of the user, when worn, thereby supporting the ankle of the user against stresses imposed on the ankle during sports activities due to overpronation and underpronation.

2. A sock, according to claim 1, characterized in that the asymmetric O-ring bandage (22) is positioned below the first ankle area of the leg part of the user on the inside of the ankle of the user and above the second ankle area of the leg part on the outside of the ankle of the user, when worn.

3. A sock, according to claim 2, characterized in that two O-ring bandages (22) are provided.

4. A sock, according to claim 1, characterized in that the asymmetric O-ring bandage (22) is positioned above the first ankle area of the leg part on the inside of the ankle of the user and below the second ankle area of the leg part on the outside of the ankle of the user, when worn.

5. A sock, according to claim 4, characterized in that two O-ring bandages (22) are provided.

6. A sock, according to claim 1, characterized in that two O-ring bandages (22) are provided.

7. A sock, according to claim 6, characterized in that the O-ring bandages (22) are arranged opposite each other.

8. A sock according to claim 7, characterized in that the O-ring bandages (22) are connected to each other by a web (24).

9. A sock, according to claim 6, characterized in that the O-ring bandages (22) are connected to each other by a web (24).

10. A sock, according to claim 6, characterized in that the bandages (22) are made of elastane.

* * * * *